United States Patent
Park et al.

(10) Patent No.: US 11,369,934 B2
(45) Date of Patent: Jun. 28, 2022

(54) FLUIDIZED BED REACTOR

(71) Applicant: LG CHEM, LTD., Seoul (KR)

(72) Inventors: Hong Seok Park, Daejeon (KR); Jae Hyung Choi, Daejeon (KR); Young Seok Ryou, Daejeon (KR); Jun Seon Choi, Daejeon (KR); Sung Jin Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 14 days.

(21) Appl. No.: 17/256,573

(22) PCT Filed: Aug. 11, 2020

(86) PCT No.: PCT/KR2020/010585
§ 371 (c)(1),
(2) Date: Dec. 28, 2020

(87) PCT Pub. No.: WO2021/060698
PCT Pub. Date: Apr. 1, 2021

(65) Prior Publication Data
US 2021/0370256 A1    Dec. 2, 2021

(30) Foreign Application Priority Data

Sep. 24, 2019   (KR) .................. 10-2019-0117211

(51) Int. Cl.
*B01J 8/24* (2006.01)
*B01J 8/00* (2006.01)
*B01J 8/38* (2006.01)
*C07C 253/26* (2006.01)

(52) U.S. Cl.
CPC .............. *B01J 8/388* (2013.01); *B01J 8/004* (2013.01); *B01J 8/006* (2013.01); *B01J 8/24* (2013.01); *C07C 253/26* (2013.01); *B01J 2208/00902* (2013.01)

(58) Field of Classification Search
CPC ... B01J 8/388; B01J 8/004; B01J 8/006; B01J 8/24; B01J 2208/00902; B01J 8/0055; B01J 8/1827; B01J 8/1836; B01J 8/1872; B01J 2208/00141; B01J 8/228; B01J 2208/00654; B01J 2208/00938; B01J 2208/00991; B01J 2208/00893; C07C 253/26; C07C 255/08
USPC ........................................................ 422/144
See application file for complete search history.

(56) References Cited

U.S. PATENT DOCUMENTS

| | | | |
|---|---|---|---|
| 4,933,149 A | 6/1990 | Rhee et al. | |
| 6,649,130 B1 | 11/2003 | Zhou et al. | |
| 2007/0199887 A1 | 8/2007 | Boer et al. | |

FOREIGN PATENT DOCUMENTS

| | | |
|---|---|---|
| CN | 201454508 U | 5/2010 |
| CN | 101293637 B | 6/2010 |
| CN | 104587911 B | 2/2017 |
| CN | 109046186 A | 12/2018 |

(Continued)

*Primary Examiner* — Huy Tram Nguyen
(74) *Attorney, Agent, or Firm* — Dentons US LLP

(57) ABSTRACT

The present invention relates to a fluidized bed reactor. The fluidized bed reactor includes: a catalyst bed; a dust collector provided in an upper portion of the fluidized bed reactor collecting catalyst particles in a gas discharged toward the upper portion of the fluidized bed reactor; and a filter portion provided in a region between the dust collector and the catalyst bed, wherein the filter portion includes a filtering screen and a plurality of conical caps coupled to the filtering screen.

11 Claims, 3 Drawing Sheets

(56) References Cited

FOREIGN PATENT DOCUMENTS

| | | |
|---|---|---|
| JP | 2016-210740 A | 12/2016 |
| JP | 2019081725 A | 5/2019 |
| JP | 2019-156737 A | 9/2019 |
| KR | 10-2003-0089016 A | 11/2003 |
| KR | 10-1586879 A | 1/2016 |
| KR | 10-2016-0036305 A | 4/2016 |
| KR | 10-2017-0023847 A | 3/2017 |
| KR | 10-2018-0078333 A | 7/2018 |
| KR | 10-2000899 B1 | 7/2019 |
| WO | 2017069722 A1 | 4/2017 |

[FIG. 1]
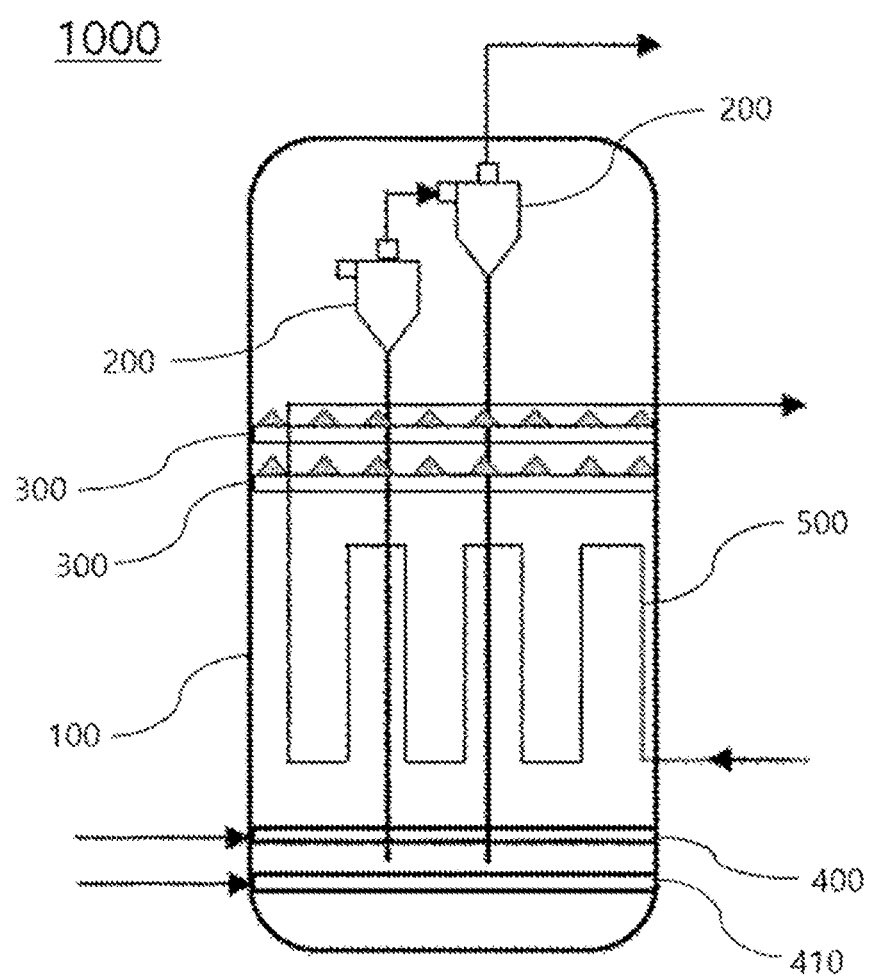

[FIG. 2]
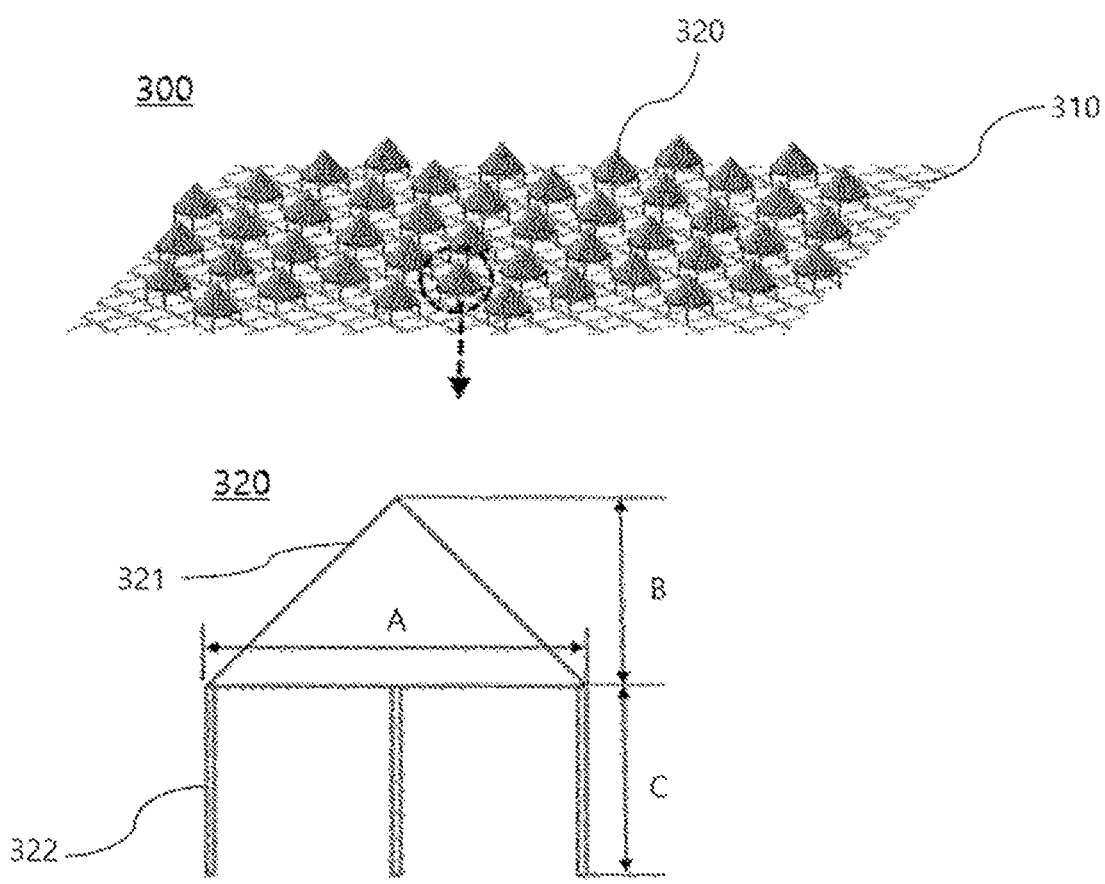

[FIG. 3]
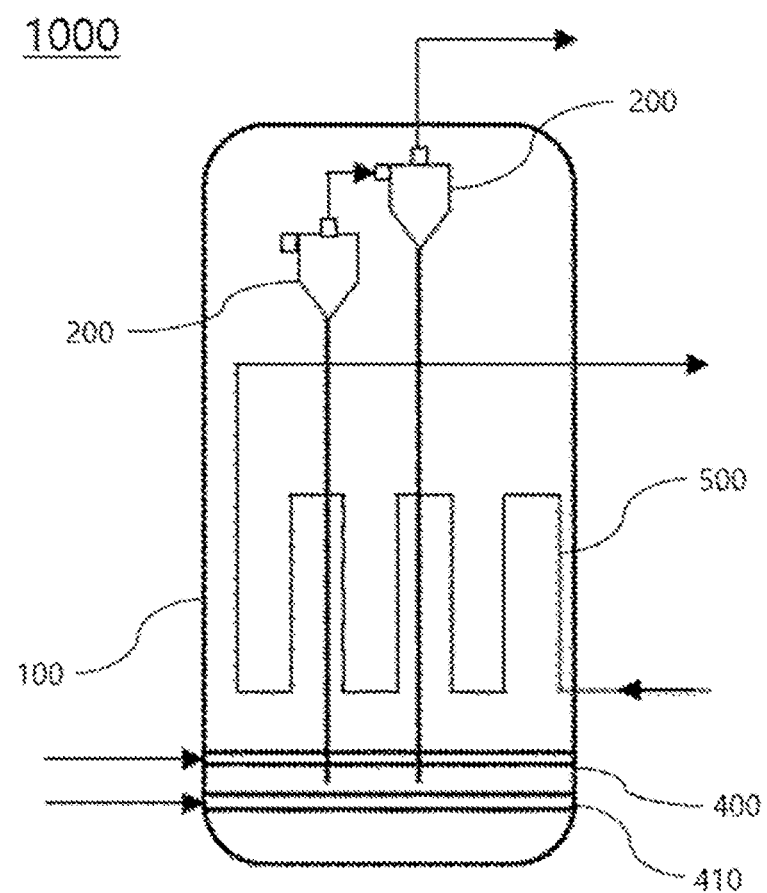

FLUIDIZED BED REACTOR

The present application is a National Phase entry pursuant to 35 U.S.C. § 371 of International Application No. PCT/KR2020/010585 filed on Aug. 11, 2020, and claims the priority to and the benefit of Korean Patent Application No. 10-2019-0117211, filed on Sep. 24, 2019, the disclosures of which in their entirety are incorporated herein by reference.

FIELD

The present invention relates to a fluidized bed reactor, and more particularly, to a fluidized bed reactor including a filter portion for collecting a fine catalyst.

BACKGROUND

A fluidized bed reactor has been used for various industrial reactions. For example, a nitrile compound such as acrylonitrile has been industrially produced by ammoxidation of a hydrocarbon such as propylene. As a method of producing a nitrile compound, a method of carrying out a gas-phase ammoxidation reaction in the presence of a metal oxide catalyst has been generally known. As for the gas-phase ammoxidation reaction, a hydrocarbon that is a raw material, ammonia, and oxygen-containing gas such as air may be put into a reactor to carry out an ammoxidation reaction in the presence of the metal oxide catalyst, thereby producing a nitrile compound.

In the fluidized bed reactor, a catalyst bed is filled with a catalyst, gases such as propylene, ammonia, air, and oxygen are sprayed at a lower portion, the sprayed gaseous components are subjected to an ammoxidation reaction while passing through the catalyst bed, and a stream containing a product obtained by the ammoxidation reaction is discharged as a stream toward an upper portion of the fluidized bed reactor.

Here, when the stream containing the product is discharged toward the upper portion of the fluidized bed reactor, since a linear velocity of the stream rising to the upper portion of the fluidized bed reactor is high, fine catalyst particles such as a large amount of fine dust are discharged toward the upper portion of the fluidized bed reactor together with the stream rising upward.

To prevent such a problem, a dust collector is installed in the fluidized bed reactor to collect the fine catalyst particles, and a stream containing the collected particles is re-supplied to the catalyst bed through a dipleg.

However, since the stream that is re-supplied to the catalyst bed contains the product in addition to the fine catalyst particles, coke is formed due to the product, which is problematic. In addition, the collected catalyst is not subjected to the ammoxidation reaction, but is maintained at a reduced state, which causes a reduction in yield of the product.

The present invention has been made in an effort to solve the problems mentioned in the background art, a fluidized bed reactor for increasing the yield of a product by minimizing a loss of fine catalyst particles and increasing catalytic activity may be provided.

That is, an object of the present invention is to reduce fine catalyst particles escaping toward an upper portion of a fluidized bed reactor and prevent coke from being formed by providing a filter portion below a dust collector provided in the fluidized bed reactor.

According to an embodiment of the present invention for solving the above-described problems, the present invention provides a fluidized bed reactor including: a catalyst bed; a dust collector provided in an upper portion of the fluidized bed reactor and collecting catalyst particles in a gas discharged toward the upper portion of the fluidized bed reactor; and a filter portion provided in a region between the dust collector and the catalyst bed, wherein the filter portion includes a filtering screen and a plurality of conical caps coupled to the filtering screen.

The fluidized bed reactor according to the present invention may include the filter portion provided below the dust collector to effectively collect fine catalyst particles escaping toward the upper portion of the fluidized bed reactor, and may re-supply the collected fine catalyst particles to the catalyst bed to increase catalyst activity and the yield of a product.

In addition, according to the present invention, the filter portion is installed below the dust collector, such that it is possible to minimize an influence on a behavior of a stream moving from a lower portion of the fluidized bed reactor to the upper portion of the fluidized bed reactor, and minimize the fine catalyst particles discharged toward the upper portion.

According to the present invention, the amount of fine catalyst particles collected by the dust collector and the amount of product are reduced to minimize the amount of stream re-supplied from the dust collector to the catalyst layer, thereby suppressing formation of coke.

BRIEF DESCRIPTION OF DRAWINGS

FIG. 1 is a schematic diagram illustrating a configuration of a fluidized bed reactor according to an embodiment.

FIG. 2 is a schematic enlarged diagram illustrating a filter portion included in the fluidized bed reactor according to the embodiment, and a conical cap.

FIG. 3 is a schematic diagram illustrating a configuration of a fluidized bed reactor according to a comparative example.

DETAILED DESCRIPTION

Terms and words used in the present invention and claims are not to be construed as a general or dictionary meaning but are to be construed as meanings and concepts meeting the technical ideas of the present invention based on a principle that the inventors can appropriately define the concepts of terms in order to describe their own inventions in the best mode.

A term "stream" in the present invention may mean a flow of fluid in a process, or may mean a fluid itself flowing in a pipe. Specifically, the "stream" may mean both a fluid itself flowing in a pipe connecting respective devices, and a flow of the fluid. Further, the fluid may mean a gas or liquid.

Hereinafter, the present invention will be described in more detail with reference to FIGS. 1 and 2 to assist in understanding of the present invention.

According to the present invention, a fluidized bed reactor 1000 is provided. The fluidized bed reactor 1000 may include: a catalyst bed 100; a dust collector 200 provided in an upper portion of the fluidized bed reactor 1000 collecting catalyst particles in a gas discharged toward the upper portion of the fluidized bed reactor 1000; and a filter portion 300 provided in a region between the dust collector 200 and the catalyst bed 100, in which the filter portion 300 may include a filtering screen 310 and a plurality of conical caps 320 coupled to the filtering screen 310 (FIG. 2).

According to an embodiment of the present invention, the fluidized bed reactor 1000 may be used in various processes. For example, the fluidized bed reactor 1000 may be used in a process of producing acrylonitrile using an ammoxidation reaction of supplied propylene.

Specifically, the catalyst bed 100 is provided in the fluidized bed reactor 1000, and gases such as propylene, ammonia, air, and oxygen are sprayed upward from a lower portion of the fluidized bed reactor 1000, and the gas stream is subjected to the ammoxidation reaction while passing through the catalyst bed 100. Acrylonitrile may be produced as a product obtained by the ammoxidation reaction. The product obtained by the ammoxidation reaction passes through the catalyst bed 100, moves to the upper portion of the fluidized bed reactor 1000, and is discharged as a stream discharged toward the upper portion of the fluidized bed reactor 1000.

An operating pressure of the fluidized bed reactor 1000 may be 1 bar to 4 bar. For example, the operating pressure of the fluidized bed reactor 1000 may be 1 bar to 3.5 bar, 1 bar to 3 bar, or 1.5 bar to 2.5 bar. Further, an operating temperature of the fluidized bed reactor 1000 may be 400° C. to 460° C. For example, the operating temperature of the fluidized bed reactor 1000 may be 410° C. to 450° C., 415° C. to 445° C., or 420° C. to 440° C. The fluidized bed reactor 1000 may be operated under the above-described condition to carry out the ammoxidation reaction of propylene.

According to an embodiment of the present invention, the catalyst bed 100 may be filled with metal oxide catalyst particles. The metal oxide catalyst particles may include, for example, one or more metals selected from the group consisting of Mo, Bi, Fe, Co, and K.

An average size of the catalyst particles may be 150 µm or less. For example, the average size of the catalyst particles may be 50 µm to 150 µm, 60 µm to 130 µm, or 70 µm to 110 µm. The catalyst bed 100 may be filled with catalyst particles having an average size within the above range for a large surface area, thereby promoting the ammoxidation reaction of propylene.

The catalyst particles that fill the catalyst bed 100 may include fine catalyst particles. For example, an average size of the fine catalyst particles may be 40 µm or less. For example, the average size of the fine catalyst particles may be 1 µm to 40 µm, 1 µm to 30 µm, or 10 µm to 30 µm.

Since a linear velocity of the stream rising to the upper portion of the fluidized bed reactor 1000 is high, fine catalyst particles having an average size within the above range are discharged toward the upper portion of the fluidized bed reactor 1000 together with the stream. To prevent such a problem, according to the related art, the dust collector 200 is installed in the fluidized bed reactor 1000 to collect fine catalyst particles, and a stream containing the collected particles is re-supplied to the catalyst bed 100 through a dipleg.

However, since the stream that is re-supplied to the catalyst bed 100 contains the product in addition to the fine catalyst particles, coke is formed due to the product, which is problematic. In addition, the collected catalyst is not subjected to the ammoxidation reaction, but is maintained at a reduced state, which causes a reduction in yield of the product.

In this regard, according to the present invention, the filter portion 300 to be described later may be provided in a region between the dust collector 200 and the catalyst bed 100 to effectively collect the fine catalyst particles escaping toward the upper portion of the fluidized bed reactor 1000, and the collected fine catalyst particles may be re-supplied to the catalyst bed 100, thereby increasing a catalyst activity and the yield of the product. Further, the amount of the stream re-supplied to the catalyst bed 100 may be minimized to suppress formation of coke.

According to an embodiment of the present invention, the fluidized bed reactor 1000 may include a first spraying portion 400 configured to spray a mixed gas containing propylene and ammonia and provided in the lower portion of the fluidized bed reactor 1000. The first spraying portion 400 may include separate pipes for supplying the propylene and the ammonia, respectively. The pipe for supplying a propylene stream and the pipe for supplying an ammonia stream may be coupled to each other at an arbitrary region, and the propylene stream and the ammonia stream may be supplied into the fluidized bed reactor 1000 through a main pipe in a next region of the region where the pipes are coupled to each other.

The main pipe connected to the inside of the fluidized bed reactor 1000 may be freely designed to have a position and shape in accordance with the size and shape of the fluidized bed reactor 1000.

The first spraying portion 400 may include a spraying nozzle connected to the main pipe. The spraying nozzle may spray, toward the upper portion of the fluidized bed reactor 1000, the mixed gas stream containing propylene and ammonia and supplied through the main pipe.

A plurality of spraying nozzles may be provided on the main pipe while being spaced apart from each other at a predetermined interval.

A spraying pressure of the spraying nozzle included in the first spraying portion 400 may be 3 bar to 8 bar. For example, the spraying pressure of the spraying nozzle may be 4 bar to 7 bar, 4.5 bar to 6.5 bar, or 5 bar to 6 bar.

According to an embodiment of the present invention, the fluidized bed reactor 1000 may include a second spraying portion 410 configured to spray air and provided in a region below the first spraying portion 400. For example, the air may mean oxygen ($O_2$). The second spraying portion 410 may include a pipe for supplying an air stream. The air stream may be supplied into the fluidized bed reactor 1000 through the pipe. The pipe connected to the inside of the fluidized bed reactor 1000 may be freely designed to have a position and shape in accordance with the size and shape of the fluidized bed reactor 1000.

The second spraying portion 410 may include a spraying nozzle connected to the pipe. The spraying nozzle may spray, toward the upper portion of the fluidized bed reactor 1000, the air stream supplied through the main pipe.

A plurality of spraying nozzles may be provided on the pipe while being spaced apart from each other at a predetermined interval.

A spraying pressure of the spraying nozzle included in the second spraying portion 410 may be 3 bar to 8 bar. For example, the spraying pressure of the spraying nozzle may be 4 bar to 7 bar, 4.5 bar to 6.5 bar, or 5 bar to 6 bar.

According to an embodiment of the present invention, a linear velocity of each of the mixed gas stream containing propylene and ammonia, and the air stream that is discharged toward the upper portion of the fluidized bed reactor 1000 through the first spraying portion 400 and the second spraying portion 410, respectively, may be 20 cm/s to 80 cm/s. For example, a linear velocity of a stream discharged toward the upper portion of the fluidized bed reactor 1000 through each of the first spraying portion 400 and the second spraying portion 410 may be 30 cm/s to 70 cm/s, 35 cm/s to 65 cm/s, or 40 cm/s to 60 cm/s.

The mixed gas stream containing propylene and ammonia, and the air stream that are discharged toward the upper portion of the fluidized bed reactor 1000 through the first spraying portion 400 and the second spraying portion 410, respectively, are supplied to the catalyst bed 100 at a linear velocity of 20 cm/s to 80 cm/s, pass the catalyst bed 100, and move to above the catalyst bed 100 together with the fine catalyst particles that fill the catalyst bed 100. When the mixed gas stream, the air stream, and a stream containing the fine catalyst particles moved to above the catalyst bed 100 pass through the filter portion 300 to be described later, the fine catalyst particles in the stream may be collected. Fine catalyst particles that are not collected by the filter portion 300 may be separated by the dust collector 200. As a result, it is possible to prevent the fine catalyst particles from being discharged as a stream discharged toward the upper portion of the fluidized bed reactor 1000.

According to an embodiment of the present invention, the filter portion 300 may be provided in the region between the dust collector 200 and the catalyst bed 100, and may collect and separate the fine catalyst particles contained in the stream moving toward the upper portion of the fluidized bed reactor 1000.

Two or more filter portions 300 may be provided at different heights. For example, the filter portion 300 may be installed at a height between a height at which the dust collector 200 of the fluidized bed reactor 1000 is installed and a height at which the uppermost end of the catalyst bed 100 is positioned, and the number of installed filter portions 300 may be freely adjusted depending on the size and shape of the fluidized bed reactor 1000, and the amount of supplied stream. For example, two to five filter portions 300 may be provided at different heights in the fluidized bed reactor 1000. For example, two or three filter portions 300 may be installed.

For example, in a case where two filter portions 300 are installed at different heights in the fluidized bed reactor 1000, it may be possible to more effectively collect the fine catalyst particles in the stream moving toward the upper portion of the fluidized bed reactor 1000. Further, in a case where two filter portions 300 are installed at different heights in the fluidized bed reactor 1000, the conical caps 320 installed in each filter portion 300 may be arranged so as not to be positioned on the same vertical line. In this case, it is possible to minimize an influence on a behavior of the stream moving toward the upper portion of the fluidized bed reactor 1000.

The filter portion 300 may include the filtering screen 310 and the plurality of conical caps 320 coupled to the filtering screen 310.

The filtering screen 310 may have a mesh form having a size of 5 cm to 20 cm. For example, the mesh size of the filtering screen 310 may be 6 cm to 18 cm, 7 cm to 15 cm, or 8 cm to 13 cm. As the filtering screen 310 having the mesh size within the above range is installed, it is possible to minimize an influence on a behavior of the stream moving toward the upper portion of the fluidized bed reactor 1000.

The mesh form of the filtering screen 310 is formed using stainless steel wires, and an average diameter of the wires may be 1 mm to 5 mm. For example, the average diameter of the wires forming the filtering screen 310 may be 1 mm to 4 mm, 1 mm to 3 mm, or 2 mm to 3 mm. In a case of forming the filtering screen 310 by using the stainless steel wires having the above average diameter, it is possible to prevent corrosion in the fluidized bed reactor 1000, and minimize an influence on a behavior of the stream moving toward the upper portion of the fluidized bed reactor 1000.

The plurality of conical caps 320 may be provided on the filtering screen 310 while being spaced apart from each other at a predetermined interval. For example, the number of conical caps 320 may be freely adjusted depending on the size and shape of the fluidized bed reactor 1000.

The conical cap 320 may include a collecting portion 321 in a hollow cone shape collecting the catalyst particles in the gas discharged toward the upper portion of the fluidized bed reactor 1000; and a plurality of connecting portions 322 provided at a predetermined interval along a circumference of the collecting portion 321 and coupled to the filtering screen 310. A form in which the filtering screen 310 and the conical cap 320 are coupled to each other is not particularly limited.

A bottom surface of the cone shape of the conical cap 320 may have an average diameter A of 20 mm to 40 mm, a height B from a vertex of the cone shape in a vertical direction may be 5 mm to 25 mm, and a length C of the connecting portion 322 may be 10 mm to 50 mm.

For example, the average diameter A of the bottom surface of the cone shape may be 23 mm to 40 mm, 23 mm to 38 mm, or 25 mm to 35 mm. Further, the height B from the vertex of the cone shape in the vertical direction may be 5 mm to 20 mm, or 10 mm to 20 mm. Further, the length C of the connecting portion 322 may be 10 mm to 45 mm, 13 mm to 45 mm, or 15 mm to 50 mm. In a case where the average diameter A of the bottom surface of the cone shape, the height B from the vertex of the cone shape in the vertical direction, and the length C of the connecting portion 322 in the conical cap 320 are within the above ranges, respectively, it is possible to minimize an influence on a behavior of the stream moving toward the upper portion of the fluidized bed reactor 1000, and effectively collect the catalyst particles contained in the stream.

As described above, the catalyst particles collected in the collecting portion 321 may be fine catalyst particles having the average size of 40 μm or less. The fine catalyst particles collected in the collecting portion 321 may fall to the catalyst bed 100 again. As a result, the fine catalyst particles that are not subjected to an ammoxidation reaction of a reactant and remain at an activated state may be reused, thereby increasing the yield of the product.

The plurality of conical caps 320 may each have a different height. Here, the height of the conical cap 320 may correspond to a sum of the height B from the vertex of the cone shape in the vertical direction and the length C of the connecting portion 322. As such, as the plurality of conical caps 320 coupled to the filtering screen 310 are designed to each have a different height, it is possible to minimize a change in flow and flow rate of the stream moving upward caused by a reduction in cross-sectional area in the fluidized bed reactor 1000.

According to an embodiment of the present invention, the dust collector 200 may be installed in a region above the filter portion 300 to collect fine catalyst particles that are not collected by the filter portion 300 among fine catalyst particles contained in the stream moving toward the upper portion of the fluidized bed reactor 1000. For example, the dust collector 200 may be a cyclone dust collector.

Two or more dust collectors 200 may be installed at different heights in the region above the filter portion 300. Here, an exhaust gas may be discharged through an upper portion of the dust collector 200 positioned in the uppermost portion of the fluidized bed reactor 1000.

According to an embodiment of the present invention, the fine catalyst particles collected by the dust collector 200 may be re-supplied to the catalyst bed 100. Specifically, according to the present invention, a re-supply line (not illustrated) connected between the dust collector 200 and the catalyst bed 100 may be provided, and the stream containing the fine catalyst particles collected by the dust collector 200 may be re-supplied to the catalyst bed 100 through the re-supply line. As a result, the fine catalyst particles that are not subjected to an ammoxidation reaction of a reactant and are remained at an activated state may be reused, thereby increasing the yield of the product.

According to an embodiment of the present invention, the fluidized bed reactor 1000 may include a cooling pipe 500 that passes through the catalyst bed 100 in the fluidized bed reactor 1000 and is configured to control a temperature by cooling an ammoxidation reactant in the fluidized bed reactor 1000. Cooling water may be supplied to the cooling pipe 500. As a result, an ammoxidation reaction of a reactant in the fluidized bed reactor 1000 may be carried out at a predetermined temperature.

Although the fluidized bed reactor according to the present invention has been described above and illustrated in the drawings, in the above description and the drawings, only the main configuration for assisting in understanding of the present invention have been described and illustrated. In addition to the processes and devices described above and illustrated in the drawings, processes and devices that are not separately described and illustrated may be appropriately applied and used to implement a particle homogenizing device according to the present invention.

The invention claimed is:

1. A fluidized bed reactor comprising:
   catalyst bed;
   a dust collector provided in an upper portion of the fluidized bed reactor collecting catalyst particles in a gas discharged toward the upper portion of the fluidized bed reactor; and
   a filter portion provided in a region between the dust collector and the catalyst bed,
   wherein the filter portion includes a filtering screen and a plurality of conical caps coupled to the filtering screen.

2. The fluidized bed reactor of claim 1, wherein the conical cap includes:
   a collecting portion in a hollow cone shape collecting the catalyst particles in the gas discharged toward the upper portion of the fluidized bed reactor; and
   a plurality of connecting portions provided at a predetermined interval along a circumference of the collecting portion and coupled to the filtering screen.

3. The fluidized bed reactor of claim 2, wherein an average size of the catalyst particles collected by the collecting portion is 40 μm or less.

4. The fluidized bed reactor of claim 2, wherein in the collecting portion, an average diameter of a bottom surface of the cone shape is 20 mm to 40 mm, a height from a vertex of the cone shape in a vertical direction is 5 mm to 25 mm, and a length of the connecting portion is 10 mm to 50 mm.

5. The fluidized bed reactor of claim 1, wherein a mesh size of the filtering screen is 5 cm to 20 cm.

6. The fluidized bed reactor of claim 1, wherein the plurality of conical caps each have a different height.

7. The fluidized bed reactor of claim 1, wherein two or more filter portions are provided at different heights.

8. The fluidized bed reactor of claim 1, wherein the fluidized bed reactor is used in a process of producing acrylonitrile using an ammoxidation reaction of supplied propylene.

9. The fluidized bed reactor of claim 1, further comprising a first spraying portion configured to spray a mixed gas containing propylene and ammonia provided in a lower portion of the fluidized bed reactor.

10. The fluidized bed reactor of claim 9, further comprising a second spraying portion configured to spray air provided in a region below the first spraying portion.

11. The fluidized bed reactor of claim 1, further comprising a re-supply line connected between the dust collector and the catalyst bed supplying a stream containing a catalyst collected by the dust collector to the catalyst bed.

* * * * *